United States Patent [19]

Brantl et al.

[11] Patent Number: 4,707,475

[45] Date of Patent: Nov. 17, 1987

[54] AGENT FOR LOWERING SERUM PROLACTIN LEVELS

[75] Inventors: Victor Brantl, Wiesbaden; Werner Bomann, Ingelheim am Rhein; Herbert Schill, Appenheim, all of Fed. Rep. of Germany

[73] Assignee: Boehringer Ingelheim KG, Ingelheim am Rhein, Fed. Rep. of Germany

[21] Appl. No.: 821,924

[22] Filed: Jan. 23, 1986

[30] Foreign Application Priority Data

Jan. 25, 1985 [DE] Fed. Rep. of Germany ....... 3502365

[51] Int. Cl.$^4$ .............................................. A61K 31/55
[52] U.S. Cl. ................................................... 514/215
[58] Field of Search ........................................ 514/215

[56] References Cited

U.S. PATENT DOCUMENTS 3,907,996 9/1975 Griss et al. ........................... 514/215
4,259,342 3/1981 Benedikter et al. ................. 514/215

Primary Examiner—Jerome D. Goldberg
Attorney, Agent, or Firm—David E. Frankhouser; Mary-Ellen M. Timbers; Alan R. Stempel

[57] ABSTRACT

Disclosed is a method of lowering the prolactin level in the blood or serum of a person which method comprises administering a therapeutically effective amount of 2-amino-6-allyl-5,6,7,8-tetrahydro-4H-thiazolo-[5,4-d]azepine or a non-toxic, pharmaceutically acceptable acid addition salt thereof.

7 Claims, No Drawings

AGENT FOR LOWERING SERUM PROLACTIN LEVELS

Belgian Pat. Nos. 684,415 and 771,330 describe, inter alia, thiazole and oxazole derivatives of formula I

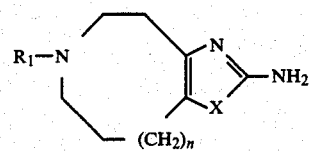

wherein $R_1$ represents a hydrogen atom, a $C_1$-$C_4$ alkyl group which can optionally be hydroxy substituted, a benzyl group which can optionally be halogen, methyl or methoxy substituted or an allyl group;

n represents the number 2 or, if X represents a sulphur atom, also the number 1; and X represents an oxygen or sulphur atom, and the physiologically acceptable acid addition salts thereof with inorganic or organic acids.

It is known from Belgian Pat. Nos. 684,415 and 771,330 that the compounds of formula I and the non-toxic, pharmaceutically acceptable acid addition salts thereof have valuable pharmacological properties. The compounds described in Belgian Pat. No. 684,415 have, in particular, an analgesic, sedative, antitussive, antipyretic and antiphlogistic activity and the compounds described in Belgian Pat. No. 771,330, depending on their substition, have a hypotensive, sedative, antitussive and/or antiphlogistic activity.

In particular, the thiazole derivatives of formula I wherein $R_1$ represent a $C_1$-$C_4$ alkyl group or an allyl group, n represents the number 2 and X represents a sulphur atom, have a hypotensive activity. Also, the oxazole derivatives of formula I wherein $R_1$ represents a hydrogen atom, a $C_1$-$C_4$ alkyl group optionally substituted by a hydroxy group, or an allyl group, n represents the number 2 and X represents an oxygen atom, have antitussive properties.

It is known from No. EP-A1-0 005 732 that the compounds of formula I above wherein n represents the number 2 also have an anti-angina activity.

For medical use, only the endogenous administration of these compounds as described in BE-PS No. 771,330 and BE-PS No. 684,415 and also in EP-AL No. 0 005 732.

It is also known from U.S. Pat. No. 4,400,378 that the compounds of formula I also have an antiglaucoma activity.

Anden et al., Naunyn-Schmiedeberg's Arch. Pharmacol., 321: 100-104 (1982) discloses that 6-allyl-2-amino-5,6,7,8-tetrahydro-4H-thiazolo-[4,5-d]azepine dihydrochloride (hereinafter referred to as B-HT 920) has a selective agonistic effect on dopamine autoreceptors (DA-autoreceptors).

Anden et al., Acta Pharmacol et Toxicol., 52: 51-56 (1983) discloses that B-HT 920 used in vivo inhibits endogenous dopamine synthesis in the brain. Dopamine is a key substance in regulating the hormone prolactin (PRL) and is the so-called "prolactin inhibiting factor" (PIF), i.e. dopamine (=PIF) or other dopamine agonists inhibit the release of PRL from the hypophysis. A reduction in dopamine results in excessive PRL secretion, since the inhibiting factor is not present (Selecta, No. 46:4344 (Nov. 15, 1982).

Gudelsky, European Journal of Pharmacology 90: 423,425 (1983) discloses that the DA-autoreceptor agonists TL-99 and 3-PPP, known from the literature, have a prolactin inhibiting activity.

However, TL-99, and 3-PPP and even the DA-autoreceptor agonist apomorphine are not capable of comparison with B-HT 920, since these substances are not selectively active as DA-autoreceptor agonists. Gudelsky et al., supra, report that TL-99 and 3-PPP act preferentially as DA agonists, i.e. not as selective DA-autoreceptor agonists. Pastor et al report in Europ. J. Pharmacol. 87: 459-464 (1983) suggests that TL-99 possibly has a postsynaptic activity, i.e. an effect on the DA-receptors. Furthermore, the stereoisomers of the substance 3-PPP have different effects on the different DA-receptors. (Koch et al., Eur. J. Pharmacol., 92: 279-283 (1983). As is well known, apomorphine also acts both on DA-receptors and also on DA-autoreceptors.

Goodale et al., Science, vol. 210, 5 December 1980, suggests that a substance which has a postsynaptic activity is indicated for the treatment of hyperprolactines.

Suprisingly, it has now been found that 6-allyl-2-amino-5,6,7,8-tetrahydro-4H-thiazolo-[4,5-d]azepine (hereinafter referred to as compound A) and the non-toxic, pharmaceutically acceptable acid addition salts thereof with inorganic or organic acids lower the blood and serum levels of prolactin (PRL).

In order to lower the PRL level in blood, compound A and the non-toxic, pharmaceutically acceptable acid addition salts thereof can be incorporated in conventional galenic preparations for oral, parenteral, rectal or transdermal administration. The single dose for oral administration in man is normally between 2.5 μg, and 350 μg, preferably between 100 μg and 250 μg; for multiple administration (e.g. 3 times a day) the daily doses may range from 15-900 μg, preferably from 30-750 μg. The parenteral and rectal doses may be of the same order of magnitude as the quantities of substance to be administered by oral route.

In view of their PRL-lowering properties, compound A and the non-toxic, pharmaceutically acceptable acid addition salts thereof, particulary B-HT 920, can be used whenever a reduction of the PRL level in the blood is indicated, particularly in the following:

1. Multiplication of PRL-producing cells (pregnancy, hyperplasia, prolactinoma);
2. Any predominance of PRL-secretion promoting factors over PIF (hypothyreosis);
3. Disorders of the menstrual cycle, such as amenorrhea with or without galactorrhea, oligomenorrhea, PRL-induced fertility disorders, corpus luteum insufficiency, premenstrual syndrome, dysmenorrhea, anovulatory cycles and post-pill amenorrhoea;
4. Cervical dysplasia
5. In the case of drug-induced blockage of the DA-receptors or inhibition of DA-secretion: combination of B-HT 920 with pharmaceuticals which are connected with an increase in PRL (e.g., neuroleptics of the phenothiazine or butyrophenone type or antiemetics such as metoclopramide);
6. Inhibition of lactation (primary and secondary weaning);
7. Puerperal mastitis; and
8. PRL-induced hypogonadism.

The following examples further describe the invention.

EXAMPLE A

The compound B-HT 920 is tested for its effect on PRL-reduction as follows. The tests are carried out with 6 healthy male subjects ranging in age from 24 to 34, each subject being given 150 μg of B-HT 920. Blood samples are taken from each subject at intervals of 0, 1, 2, 3 and 5 hours. The prolactin level in the sample is determined by the known PROLRIA-100 radioimmunological method of the National Insitute of the Radioelements, 6220 Fleurs, Belgium.

The following table contains the results found for each subject at the 1 hour intervals shown.

| TIME | SUBJECT | | | | | |
|---|---|---|---|---|---|---|
| | 1 | 2 | 3 | 4 | 5 | 6 |
| 0 | 3.33 | 3.86 | 4.22 | 5.04 | 5.00 | 6.59 |
| 1 | 2.56 | 2.85 | 4.15 | 4.52 | 7.19 | 7.59 |
| 2 | 0.52 | 0.69 | 4.92 | 7.89 | 1.37 | 1.57 |
| 3 | 2.52 | 0.52 | 1.26 | 7.19 | 3.43 | 1.39 |
| 5 | 3.26 | 2.25 | 1.85 | 4.11 | 2.89 | 4.33 |

Furthermore, compound A and the non-toxic, pharmaceutically acceptable acid addition salts thereof are well tolerated. For example, B-HT 920 administered to mice has an oral $LD_{50}$ of 455 mg/kg.

EXAMPLE I

Tablet core

Composition:

| 1 Tablet core contains: | |
|---|---|
| B-HT 920 | 50 μg |
| Lactose | 38.45 mg |
| Corn starch | 10.0 mg |
| Gelatine | 1.0 mg |
| Magnesium stearate | 0.50 mg |
| | 50.0 mg |

Method of preparation:

A mixture of the active substance with lactose and corn starch is granulated with a 10% aqueous gelatine solution through a 1 mm screen, dried at 40° C. and passed through the same screen again. The granulate thus obtained is mixed with magnesium stearate and compressed to form tablet cores. The operation must be carried out in a darkened room.

| Weight of core: | 50 mg |
|---|---|
| Die: | 5 mm, convex |

The tablet cores thus obtained are coated in known manner with a coating of sugar and talc. The finished coated tablets are polished with beeswax.

| Weight of coated tablet: | 100 mg |
|---|---|

EXAMPLE II

Suppositories

1 Suppository contains:

| B-HT 920 | 100.0 μg |
|---|---|
| Suppository mass (e.g. Witepsol W 45) | 1690.0 mg |

Method of preparation:

The finally powdered substance is stirred into the molten suppository mass, which has been cooled to 40° C., with an immersion homogenizer. At 35° C. the mass is poured into slightly chilled moulds.

EXAMPLE III

Ampoules containing 200 μg of B-HT 920

1 Ampoule contains:

| B-HT 920 | 200 μg |
|---|---|
| Citric acid | 7.0 mg |
| sec. sodium phosphate. 2 $H_2O$ | 3.0 mg |
| sodium pyrosulfite | 1.0 mg |
| Distilled water ad | 1.0 mg |

Method of preparation:

The buffer substances, active substance and sodium pyrosulfite are dissolved successively in boiled water which has been cooled under a current of $CO_2$. The solution is made up to the specified volume with boiled water and filtered free from pyrogens.

| Packaging: | in brown ampoules under protective gas |
|---|---|
| Sterilization: | 20 minutes at 120° C. |

The preparation and packaging of the ampoule solution must e carried out in a darkened room.

EXAMPLE IV

Coated tablets containing 1 mg of B-Ht 920

1 tablet core contains:

| B-HT 920 | 100 μg |
|---|---|
| Lactose | 36.0 mg |
| Corn starch | 12.4 mg |
| Gelatine | 1.0 mg |
| Magnesium stearate | 0.5 mg |
| | 50.0 mg |

Method of preparation:

| Analogously to Example I. | |
|---|---|
| Weight of core: | 50 mg |
| Die: | 5 mm, convex |
| Weight of coated tablet: | 100 mg |

EXAMPLE V

Coated tablets containing 0.2 mg of B-HT 920

1 tablet core contains:

| B-HT 920 | 0.2 mg |
|---|---|
| Digoxin | 0.25 mg |
| Lactose | 66.55 mg |
| Potato starch | 25.0 mg |
| Polyvinyl pyrrolidone | 2.0 mg |
| Magnesium stearate | 1.0 mg |

-continued

| | |
|---|---|
| | 120.0 mg |

Method of preparation:

A thorough mixture of the active substance with lactose and potato starch is granulated with a 10% solution of the polyvinyl pyrrolidone in ethanol through a 1.5 mm screen, then dried at 40° C. and passed through a 1.0 mm screen. The granulate thus obtained is mixed with magnesium stearate and compressed to form tablet cores.

| | |
|---|---|
| Weight of core: | 95 mg |
| Punch: | 7 mm, convex |

The tablet cores thus produced are coated in known manner with a coating of sugar and talc. The finished coated tablets are polished with beeswax.

| | |
|---|---|
| Weight of coated tablet: | 175 mg. |

EXAMPLE VI

Gelatine capsules containing 300 μg of B-HT 920

1 Capsule contains:

| | |
|---|---|
| B-HT 920 | 300 μg |
| Codeine phosphate | 10.0 mg |
| Tartaric acid | 3.0 mg |
| Corn starch | 86.7 mg |
| | 100.0 mg |

Method of preparation:

The substances are intensively mixed and packed into opaque capsules of suitable size.

| | |
|---|---|
| Capsule content: | 100 mg. |

We claim:

1. A method of lowering the prolactin level in the blood or serum of a person, which method comprises administering, to a person suffering from a condition or disease state treatable by reducing the prolactin level, a therapeutically effective amount of 2-amino-6-allyl-5,6,7,8-tetrahydro-4H-thiazolo-[5,4-d]azepine or a non-toxic, pharmaceutically acceptable acid addition salt thereof.

2. The method of claim 1 which comprises administering a single dose of from about 2.5 μg to about 350 μg of 2-amino-6-allyl-5,6,7,8-tetrahydro-4H-thiazolo-[5,4-d]azepine or a non-toxic, pharmaceutically acceptable acid addition salt thereof.

3. The method of claim 2 wherein said single dose is from about 100 μg to about 250 μg.

4. A method for treating amenorrhea associated with hyperprolactinemea which comprises administering to a female suffering from the same a therapeutically effective amount of 2-amino-6-allyl-5,6,7,8-tetrahydro-4H-thiazolo-[5,4-d]azepine or a non-toxic, pharmaceutically acceptable salt thereof.

5. A method for treating galactorrhea associated with hyperprolactinema which comprises administering to a female suffering from the same a therapeutically effective amount of 2-amino-6-allyl-5,6,7,8-tetrahydro-4H-thiazolo-[5,4-d]azepine or a non-toxic, pharmaceutically acceptable salt thereof.

6. A method for treating female infertility associated with hyperprolactinemea which comprises administering to a female suffering from the same a therapeutically effective amount of 2-amino-6-allyl-5,6,7,8-tetrahydro-4H-thiazolo-[5,4-d]azepine or a non-toxic, pharmaceutically acceptable salt thereof.

7. A method for inhibiting lactation associated with pregnancy which comprises administering to a lactating female a therapeutically effective amount of 2-amino-6-allyl-5,6,7,8-tetrahydro-4H-thiazolo-[5,4-d]azepine or a non-toxic, pharmaceutically acceptable salt thereof.

* * * * *